United States Patent [19]
Greenberg

[11] Patent Number: 5,358,111
[45] Date of Patent: Oct. 25, 1994

[54] HOLDER FOR USED SURGICAL NEEDLES

[76] Inventor: Anne T. Greenberg, 316 Oak Street, Winnipeg, Manitoba, Canada, R3M 3R5

[21] Appl. No.: 105,126

[22] Filed: Aug. 12, 1993

[51] Int. Cl.$^5$ ............................................. B65D 83/10
[52] U.S. Cl. ................................... 206/366; 604/263
[58] Field of Search ........... 128/DIG. 26; 223/109 R; 206/63.3, 366, 370, 440, 363; 248/176; 211/70.6; 604/263; D24/227, 229

[56] References Cited
U.S. PATENT DOCUMENTS

| | | | |
|---|---|---|---|
| 4,151,913 | 5/1979 | Freitag | 206/63.3 |
| 4,418,821 | 12/1983 | Sandel | 206/63.3 |
| 5,024,326 | 6/1991 | Sandel et al. | D24/227 |

OTHER PUBLICATIONS

Drawing by applicant and photocopy of a product by Johnson & Johnson Medical Inc. known by the Trademark "Discard-a-Pad".

*Primary Examiner*—Jerome L. Kruter
*Attorney, Agent, or Firm*—Adrian D. Battison; Stanley G. Ade; Murray E. Thrift

[57] ABSTRACT

Suture needles used in operations are stored after use on a holder which comprises a card strip having an adhesive layer across a top edge on the undersurface for attachment to a support surface and a foam strip along the top surface spaced from one side edge and spaced from the top edge. The needles are inserted into the foam material parallel to the substrate and a bare edge of the substrate from which the foam is spaced allows the substrate to be handled without contacting the foam and thus without any danger of pricking. The substrate can be cut after inserting a predetermined number of needles for example 5 needles for easy counting of the needles.

18 Claims, 2 Drawing Sheets

HOLDER FOR USED SURGICAL NEEDLES

BACKGROUND OF THE INVENTION

This invention relates to a holder for used surgical needles for use in operating theaters or the like.

Many operations require the use of a large number, even greater than 30, of separate suture needles. These separate suture needles after use must be carefully stored since they are potentially contaminated and since it is necessary to count the needles to ensure that all are properly accounted for when the operation is complete.

The conventional technique for storing the suture needles after use is simply to place them in a towel and then to extract them from the towel during the counting process. This is of course highly dangerous in view of the danger of pricking and is relatively crude and inefficient.

One prior art proposal has been to provide a strip of foam material which has an adhesive back so the foam is attached onto the top surface of a surgical drape carried over a table surface in the operating theater. The foam material thus simply acts as a replacement for the towel and it is necessary to handle the foam material carrying the needles after the operation is complete. This is highly undesirable since the foam material is attached to the drape and the foam material carries the potentially dangerous needles with the potential of pricking. The foam material has therefore found little success and generally operating theaters continue to use the towel technique which is unsatisfactory.

It is one object of the present invention, therefore, to provide an improved holder for used surgical needles.

It is a second object of the present invention to provide an improved method for handling and storing used surgical needles.

SUMMARY OF THE INVENTION

According to a first aspect of the invention there is provided a holder for used surgical needles comprising a sheet of a flexible substrate having a front surface, rear surface, a first end edge, second end edge, a first side edge and a second side edge, a strip of foam material on the front surface into which the used needles can be inserted, the strip extending along the substrate from a position adjacent the first end edge to a position adjacent the second end edge and having a width less than that of the substrate so as to be spaced from the first side edge of the substrate thus leaving a bare strip along the front surface of the substrate at the first side edge which is free from the foam material, and adhesive means on the rear surface for attachment to the substrate to a support surface.

According to a second aspect of the invention there is provided a method for storing used surgical needles comprising providing a sheet of a flexible substrate having a front surface, rear surface, a first end edge, second end edge, a first side edge and a second side edge, a strip of foam material on the front surface into which the used needles can be inserted, the strip extending along the substrate from a position adjacent the first end edge to a position adjacent the second end edge and having a width less than that of the substrate so as to be spaced from the first side edge of the substrate thus leaving a bare strip along the front surface of the substrate at the first side edge which is free from the foam material, and adhesive means on the rear surface for attachment to the substrate to a support surface, inserting the needles into the foam material so as to be supported thereby generally in a row from one end edge toward the opposed end edge, grasping the substrate by said bare strip and, after inserting a predetermined number of needles, cutting the substrate and the strip of foam material in a direction generally at right angles to the side edges to separate a portion thereof carrying the predetermined number of needles.

One embodiment of the invention will now be described in conjunction with the accompanying drawings in which:

BRIEF DESCRIPTION OF THE DRAWINGS

In the drawings like characters of reference indicate corresponding parts in the different figures.

DETAILED DESCRIPTION

Figure 1:
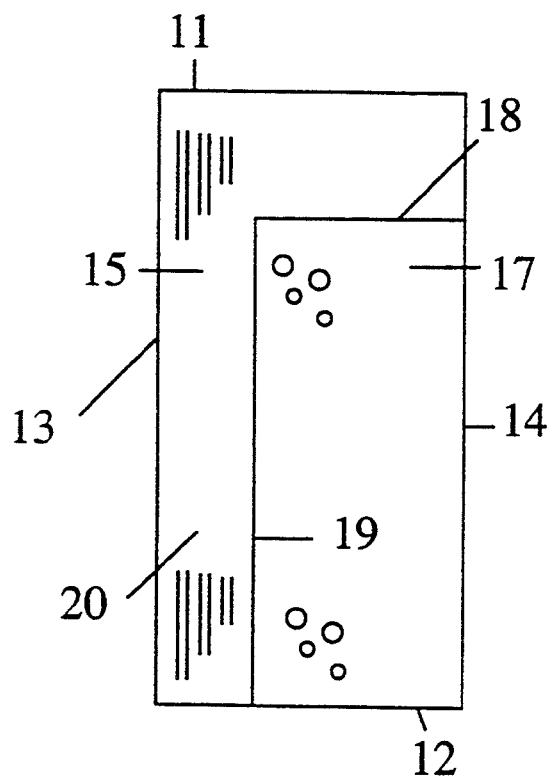
FIG. 1 is a top plan view of the holder according to the present invention.
Figure 2:
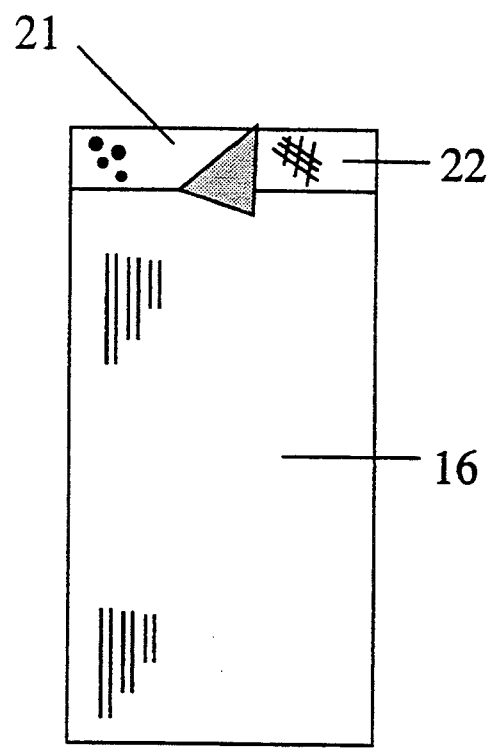
FIG. 2 is a bottom plan view of the holder of FIG. 1.
Figure 3:
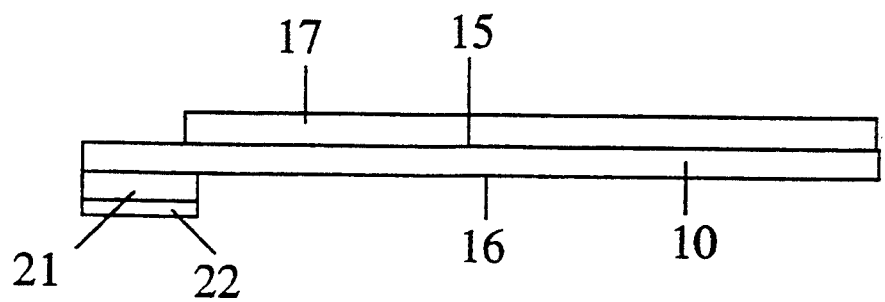
FIG. 3 is a side elevational view of the holder of FIG. 1.
Figure 4:
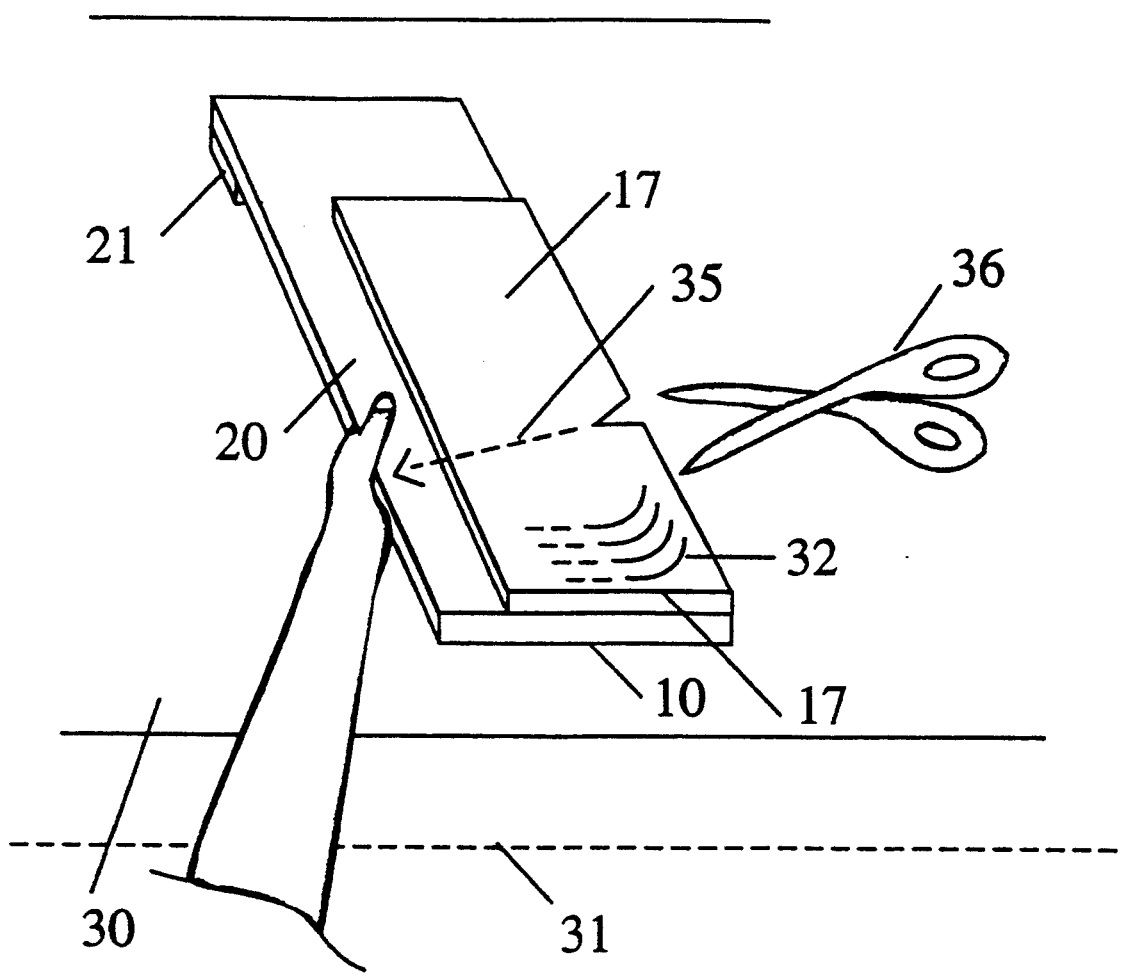
FIG. 4 is an isometric view showing schematically the holder in use.

The holder comprises a substrate 10 consisting of a single elongate flat panel of thin flexible card or the like which is cheap to manufacture, sufficiently strong to hold the foam materials in place as described hereinafter and can be readily cut as described hereinafter. The substrate 10 is rectangular and defines a first end edge 11 preferably at the top, second end edge 12 at the bottom, a first side edge 13 and a second side edge 14. The substrate further includes a front surface 15 and a rear surface 16. The substrate has attached to the front surface thereof an elongate strip of foam material 17. The strip 17 includes a top edge 18 spaced from the top edge 11 of the substrate. The strip 17 also includes one side edge lying directly above the side edge 14. An opposed side edge 19 of the strip is spaced front the side edge 13 by an elongate bare strip 20 of the substrate which is free from the foam material and this can be grasped manually.

The rear surface 16 of the substrate simply carries an adhesive strip 21 across the top edge 11. Prior to use the adhesive strip 21 carries a covering layer 22 which can be removed to expose the adhesive for attachment to a required surface.

In a preferred embodiment the length of the substrate is 15 centimeters and the length of the foam strip is 12.5 centimeters leaving a bare space of 2.5 centimeters at the top edge. The width of the foam strip is preferably 2.5 centimeters and the width of the substrate is 4.5 centimeters leaving the bare strip 20 a width of 2 centimeters.

It will be noted that the bare strip at the top of the foam strip 17 is of the same order of magnitude as or slightly greater than the width of the adhesive strip 21. The thickness of the foam material is preferably of the order of ⅛ inch which is just sufficient to receive the needles so the pointed end is properly carried within the foam material and the needles remain lying generally parallel to the substrate.

In operation, the substrate is attached adhesively to the surface of a surgical drape 30 provided on a table top 31 after, of course, removal of the covering layer 22. After use of a suture needle 32, it is simply inserted into the foam material parallel to the substrate so the pointed end is received within the foam material while the rear end remains exposed above the foam material. The needle is thus safely received and held in place securely by its frictional engagement with the foam material. After the first needle is installed, further needles are inserted in a row side by side at right angles to the length of the strip 17 up to a predetermined number of such needles. The predetermined number is generally a readily countable number such as 5 or 10. The bare strip 20 of the substrate allows the substrate to be readily grasped without in any way engaging the foam material and thus avoiding any danger of pricking from the needles. The width of the bare strip is thus such that it can be grasped by the fingers and thumb of the user as shown. The fact that the adhesive strip 21 is arranged only at the top edge allows the substrate to be lifted away slightly from the support surface by the user when required. The user can then cut the substrate along a cut line 35 using scissors 36 to separate the predetermined number of needles from the remainder of the substrate and the remainder of the foam strip. This enables the counting of the needles count to be effected very easily while the needles are maintained properly attached to a storage system without the danger of pricking. The portions of the substrate carrying the needles can be readily handled by the bare strip of the substrate.

The bare portion of the substrate at the top of the substrate ensures that no needles are inserted into the foam material at the portion aligned with the adhesive strip so that all needles can be cut away and carried on portions of the cut substrate none of which carry adhesive material.

Since various modifications can be made in my invention as herein above described, and many apparently widely different embodiments of same made within the spirit and scope of the claims without departing from such spirit and scope, it is intended that all matter contained in the accompanying specification shall be interpreted as illustrative only and not in a limiting sense.

I claim:

1. A holder for used surgical needles comprising a substrate consisting solely of a single flat panel formed of a flexible sheets material, the panel having a front surface, rear surface, a first end edge, second end edge, a first side edge and a second side edge, the panel being elongate such that the side edge thereof are longer than the end edges thereof, the sheet material being readily curable by scissors, an elongate strip means of foam material on the front surface into which the used needles can be inserted, the elongate foam strip means extending along the panel from a position adjacent the first end edge to a position adjacent the second end edge and having a width less than that of the so as to be spaced from the first side edge of the panel thus leaving an elongate bare strip of the panel along the front surface of the panel between the first side edge and the foam strip means which bare strip free from the foam material and is bare therealong allowing manual grasping of the panel by the bare strip at different positions therealong, and adhesive means on the rear surface of the panel for attachment of the panel to a support surface.

2. The holder according to claim 1 wherein the adhesive means is located only adjacent the first end edge.

3. The holder according to claim 1 wherein the foam strip means has an end edge spaced from said first end edge of the panel so as to leave a bare portion of the panel on the front surface of the panel at the first end edge which is free from the foam material.

4. The holder according to claim 1 wherein the adhesive means is located only adjacent the first end edge, wherein the foam strip means has an end edge spaced from said first end edge of the panel so as to leave a bare portion of the panel on the front surface of the panel at the first end edge which is free from the foam material and wherein the bare portion is spaced from the first end edge by a distance substantially equal to the width of the adhesive means from the first end edge.

5. The holder according to claim 1 wherein the strip of foam material is arranged along the second side edge.

6. The holder according to claim 1 wherein the thickness of the foam material is arranged to receive the surgical needle punctured therein and generally parallel thereto.

7. The holder according to claim 6 wherein the thickness of the foam material is of the order of ⅛ inch.

8. The holder according to claim 1 wherein the width of the strip means of foam material is in the order of 1 inch.

9. A method for storing used surgical needles comprising providing a sheet of a flexible substrate having a front surface, rear surface, a first end edge, second end edge, a first side edge and a second side edge, providing a strip of foam material on the front surface into which the used needles can be inserted, arranging the strip extending along the substrate from a position adjacent the first end edge to a position adjacent the second end edge providing the foam strip with a width less than that of the substrate so as to leave a bare strip on the front surface of the substrate between the first side edge and the foam strip which bare strip is free from the foam material, providing adhesive means on the rear surface, attaching by the adhesive the substrate to a support surface, inserting the needles into the foam material so as to be supported thereby generally in a row from the first end edge toward the second end edge, grasping the substrate by said bare strip and, after inserting a predetermined number of needles, coming the substrate and the foam strip in a direction generally at right angles to the side edges to separate a portion of the substrate and the foam strip carrying the predetermined number of needles.

10. The method according to claim 9 including providing the adhesive means only adjacent the first end edge.

11. The method according to claim 9 including arranging the foam strip to have an end edge spaced from said first end edge of the substrate so as to leave a bare portion of the substrate on the front surface of the substrate at the first end edge which is free from the foam material.

12. The method according to claim 9 including providing the adhesive means only adjacent the first end edge, and arranging the foam strip to have an end edge spaced from said first end edge of the substrate so as to leave a bare portion on the front surface of the substrate at the first end edge which is free from the foam material with a width of the bare portion from the first end edge being substantially equal to the width of the adhesive means from the first end edge.

13. The method according to claim 9 including arranging the strip of foam material along the second side edge.

14. The method according to claim 9 including providing a thickness of the foam material to receive the surgical needle punctured therein and generally parallel thereto.

15. The method according to claim 14 including proving a thickness of the foam material of ⅛ inch.

16. The method according to claim 9 including providing a width of the strip of foam material of 1 inch.

17. The method according to claim 9 Including providing the substrate as a single flat, elongate panel of a flexible sheet material which is readily curt able with scissors.

18. The method according to claim 17 Including arranging the foam strip as an elongate strip longitudinal of the panel and so as to define said bare strip as an elongate strip longitudinal of the panel.

* * * * *